US006248883B1

(12) United States Patent
Gorkovenko et al.

(10) Patent No.: US 6,248,883 B1
(45) Date of Patent: Jun. 19, 2001

(54) METHODS OF PURIFYING LITHIUM SALTS

(75) Inventors: Alexander Gorkovenko, Tucson, AZ (US); Grigorii L. Soloveichik, Latham, NY (US)

(73) Assignee: Moltech Corporation, Tucson, AZ (US)

( * ) Notice: Subject to any disclaimer, the term of this patent is extended or adjusted under 35 U.S.C. 154(b) by 0 days.

(21) Appl. No.: 09/205,873

(22) Filed: Dec. 4, 1998

Related U.S. Application Data

(63) Continuation-in-part of application No. 09/127,468, filed on Jul. 31, 1998, now abandoned.

(51) Int. Cl.$^7$ ........................ C07D 281/02; C07D 207/36
(52) U.S. Cl. ..................... 540/544; 540/467; 548/547; 558/44; 558/56; 562/30; 562/45; 568/23; 564/80
(58) Field of Search ................... 514/425, 431, 514/506, 553; 540/544, 467; 548/547; 558/44, 56; 562/30, 45; 564/80; 568/23

(56) References Cited

U.S. PATENT DOCUMENTS

| Re. 28,456 | * | 7/1975 | Langer, Jr. et al. ................ 260/563 |
|---|---|---|---|
| 3,562,295 | | 2/1971 | Pedersen . |
| 3,687,978 | | 8/1972 | Pedersen . |
| 3,977,900 | | 8/1976 | Luehrs . |
| 3,987,061 | | 10/1976 | Pedersen . |
| 4,308,324 | | 12/1981 | Newman . |
| 4,321,314 | | 3/1982 | Bowden et al. . |
| 4,505,997 | | 3/1985 | Armand et al. . |
| 4,659,815 | * | 4/1987 | Pacey et al. ..................... 540/467 |
| 4,880,714 | | 11/1989 | Bowden . |
| 4,895,778 | | 1/1990 | Nalewajek . |
| 4,994,110 | | 2/1991 | Stoffel et al. . |
| 5,514,493 | | 5/1996 | Waddell et al. . |
| 5,538,812 | | 7/1996 | Lee et al. . |
| 5,652,072 | | 7/1997 | Lamanna et al. . |

FOREIGN PATENT DOCUMENTS

| 2 698 631 | 6/1994 | (FR) . |
|---|---|---|
| 9-255685 | 9/1997 | (JP) . |

OTHER PUBLICATIONS

Brouillette et al., "Apparent Molar Volume, Heat Capacity, and Conductance of Lithium Bis(trifluoromethylsulfone)imide in Glymes and Other Aprotic Solvents", *J. Solution Chem.*, vol. 27, No. 2, pp. 151–182 (1998).

Choquette et al., "Sulfamides and Glymes as Aprotic Solvents for Lithium Batteries", *J. Electrochem. Soc.*, vol. 145, No. 10, pp. 3500–3507 (1998).

Cotton et al., *Advanced Inorganic Chemistry*, 3$^{rd}$ ed., pp. 199 & 917, John Wiley & Sons (1972).

Couture et al., "Some Thermodynamic and Transport Properties of Lithium Salts in Mixed Aprotic Solvents and the Effect of Water on Such Properties", *Can. J. Chem.*, vol. 74, pp. 153–164 (1996).

Dominey, "Novel Stable, Non–Complexing Anions for Rechargeable Lithium Batteries", NTIS Report No. PB 93–138741, 32 pages, U.S. Dept. of Commerce (1987).

Kita et al., "On the Characteristics of Electrolytes with New Lithium Imide Salts", *J. Power Sources*, vol. 68, pp. 307–310 (1997).

Krause et al., "Corrosion of Aluminum at High Voltages in Non–Aqueous Electrolytes Containing Perfluoroalkylsulfonyl Imides; New Lithium Salts for Lithium–Ion Cells", *J. Power Sources*, vol. 68, pp. 320–325 (1997).

Laverdure et al., "Optimization of Electrolyte Purification Procedures", Proceedings of the Symposium on Primary and Secondary Ambient Temperature Lithium Batteries, pp. 692–698, Electrochemical Society (1988).

Olsher et al., "Coordination Chemistry of Lithium Ion: A Crystal and Molecular Structure Review", *Chem. Rev.*, vol. 91, pp. 137–164 (1991).

Sandman, "Purification of Organic Materials for Electrical and Optical Studies", *J. Crystal Growth*, vol. 89, pp. 111–116 (1988).

\* cited by examiner

*Primary Examiner*—Joseph K. McKane
(74) *Attorney, Agent, or Firm*—Morrison & Foerster LLP (57) ABSTRACT

Provided are methods of purification of an organic lithium salt comprising the steps of: (a) dissolving an impure organic lithium salt in a solution comprising an organic complexing solvent; (b) crystallizing from said solution a solid solvate complex comprising said lithium salt and said organic complexing solvent; (c) separating said solid solvate complex from said solution; (d) dissociating said solid solvate complex to yield: (i) said lithium salt in a solid form, and, (ii) a volatile composition comprising said organic complexing solvent; and, (e) removing said volatile composition to yield said lithium salt in a solid form of purity greater than the purity of said impure lithium salt. The present invention also pertains to electrolytes for electric current producing cells comprising such purified lithium salts.

33 Claims, 4 Drawing Sheets

METHODS OF PURIFYING LITHIUM SALTS

CROSS REFERENCE TO RELATED APPLICATIONS

This application is a continuation-in-part of U.S. application Ser. No. 09/127,468, now abandoned, filed Jul. 31, 1998.

TECHNICAL FIELD

The present invention relates generally to the purification of ionic organic salts. More particularly this invention pertains to methods of purification of an organic lithium salt comprising the steps of: (a) dissolving an impure organic lithium salt in a solution comprising an organic complexing solvent; (b) crystallizing from said solution a solid solvate complex comprising said lithium salt and said organic complexing solvent; (c) separating said solid solvate complex from said solution; (d) dissociating said solid solvate complex to yield: (i) said lithium salt in a solid form, and, (ii) a volatile composition comprising said organic complexing solvent; and, (e) removing said volatile composition to yield said lithium salt in a solid form of purity greater than the purity of said impure lithium salt.

BACKGROUND

Throughout this application various publications, patents, and published patent applications are referred to by an identifying citation. The disclosure of the publications, patents, and published patent applications referenced in this application are hereby incorporated by reference into the present disclosure to more fully describe the state of the art to which this invention pertains.

Numerous methods are known for the purification of organic solids, as for example described in *Chemical Separation and Measurement*, Chapters 14 to 17, (1974), W. B. Saunders Company, by Peters et al., and in *Purification of Laboratory Chemicals*, 3$^{rd}$ Edition, (1988), Butterworth Heiriemann, by Perin et al. Of those methods described, crystallization has been widely used and has proven to be an effective method for the purification of solids. Crystallization can be from a single solvent or from a mixture of solvents. Other methods for the purification of solids include: sublimation; zone refining as described in *Zone Melting of Organic Compounds*, (1963), Wiley, by Herngton; and, chromatographic separation techniques, such as, column chromatography, liquid chromatography, gas chromatography, gel permeation chromatography and ion exchange chromatography. For ionic materials electrophoresis can also be used. The most appropriate method for the purification of a particular material is not always apparent without experimentation, and is dependent upon many different factors. These may include the physical properties of the material itself, such as melting point; polarity; the type and amount of impurity present in the material to be purified; and how similar or different the impurity is from the desired pure material. Other important considerations include the purity desired in the material for its particular use and the cost or complexity of the purification technique.

A limitation of crystallization as a method of purification includes the formation of solvate complexes in which solvent molecules are tightly held in the crystallized material. Likewise, the impurities in a material may co-crystallize with the material so that little if any purification is achieved. Sublimation is not applicable to many solids because the solids are not stable at the temperatures required for volatilization or they may become liquid at that temperature, and while chromatography is particularly well suited to small scale separations, such as needed for analysis, it is severely limited for large scale purifications. Furthermore, chromatographic techniques invariably use a diluent as a carrier, either a liquid or gas. In the case of liquids, these must be readily removed from the material after the impurity or impurities have been separated in the chromatographic process. For gas chromatography to be used, the material to be purified must have significant volatility and good thermal stability, which excludes its use for many types of compounds especially those of high molecular weight, with high boiling points, or with ionic salt properties.

It is critical for many ionic materials that they be absolutely free of impurities in their intended use. For example, materials used in applications where optical and electrical properties are important must be especially pure, as described, for example, by Sandman in *J. Crystal Growth*, 1988, 89, 111–116. Similarly, Stoffel et al. in U.S. Pat. No. 4,994,110 describe the negative impact of impurities, at low levels, in lithium salts of anionic dyes used in ink jet inks and describe an ion exchange process for impurity removal.

Purification of ionic salts is especially difficult in that the number of methods applicable is limited mainly to crystallization and particularly to the use of polar solvents. These solvents tend to associate strongly with the ionic material making it difficult to obtain solvent-free solids in many cases Similarly, the purity of electrolytes is critical to the performance of electrochemical cells, batteries and related electrochemical devices. While the purification of electrolyte solvents may be performed by standard methods for the purification of liquids, such as distillation, the ionic solutes, especially organic ionic solutes, are often not readily purified by such methods. Other approaches have therefore been used for the purification of ionic solutes for use in electrolytes for electrochemical cells and battery applications.

For example, U.S. Pat. No. 4,895,778 to Nalewajek describes a procedure for the removal of impurities from electrolytes, particularly metal impurities, by the use of a chelating resin. U.S. Pat. No. 4,308,324 to Newman describes a two step procedure for handling contamination in electrolytes. In this process the electrolyte is treated in the first step with a mercury/alkaline metal amalgam, followed by treatment with an oxidizing agent. In another approach, Laverdure et al., *Proceedings of the Symposium on Primary and Secondary Ambient Temperature Lithium Batteries*, Electrochemical Soc., 1988, 692–698, describe the use of alumina, lithium-mercury amalgam, sodium-potassium alloy, or lithium foil to remove impurities from electrolytes such as lithium hexafluoroarsenate in 2-methyltetrahydrofuran.

In an alternative approach to high purity electrolytes, the ionic electrolyte solute is prepared in presence of complexing solvent. For example, U.S. Pat. No. 4,880,714 to Bowden describes a method of preparation of $LiPF_6$ electrolyte salt in presence of a complexing ether solvent and isolation of the $LiPF_6$ ether complex. The solvate complex is reported to be stable and protects the ionic salt from undesirable decomposition. In a related example, U.S. Pat. No. 4,321,314 to Bowden et al. reports the formation of a very stable molecular complex between $LiClO_4$ and dimethoxyethane. This complex is reported to yield electrolyte solutions which contain no free dimethoxyethane.

Of those salts used as ionic solutes in electrolytes, the fluoroalkylsulfonylimides have proved to be particularly difficult to obtain in pure form, and in particular the lithium salts of bis(perfluoromethylsulfonyl)imide, bis (perfluoropropanesulfonyl)imide and bis (perfluorobutanesulfonyl)imide.

For example, U.S. Pat. No. 5,652,072 to Lamanna et al. reports the presence of impurities in ionic organic electrolyte salts, lithium perfluoroalkylsulfonylimides, but offers no purification process. Dominey in a report "Novel Stable, Non-Complexing Anions for Rechargeable Lithium Batteries", NTIS PB 93-138741 describes unsuccessful attempts to purify lithium bis(trifluoromethylsulfonyl)imide. In particular, the inability to obtain purification by recrystallization of the lithium bis(trifluoromethylsulfonyl)imide from dioxane is reported. Choquette et al. in *J. Electrochem. Soc.*, 1998, 3500–3507, report that attempts to purify this same lithium imide by recrystallization were unsuccessful. Japanese Patent Publication No. 09-255685, published Sep. 30, 1997, to Suzuki et al., describes a purification of perfluoroalkylsulfonylimides by crystallization from dioxane followed by dissolution of the crystals in a polar solvent of boiling point less than 100° C. After filtration to remove traces of insoluble material, the solution in the polar solvent is evaporated to recover the sulfonylimide. This process reduced the levels of sodium, potassium, calcium magnesium and sulfate impurities, however, the recovery of the pure salt was reported to be only 60%.

To be useful any purification process for the purification of ionic organic salts needs to meet a number of criteria, including: the ability to handle large scale purifications; provide high yield; handle a variety of impurities; employ standard equipment; and be applicable to several families of materials.

It is apparent that the purification methods described above meet only some of these criteria: each process fails to meet at least one criterion. There remains, therefore, a need for improved methods of purification to handle a range of impurity types in ionic organic salts especially those used in electrolytes. The need is particularly important for ionic organic salts such as perfluoroalkylsulfonylimide alkali metal salts, for example bis(trifluoromethylsulfonyl)imide lithium salt, which because of their involved manufacturing processes may contain several types of impurity, and which are needed in high purity in applications such as electrolyte salts for the electrolytes of electrochemical cells.

SUMMARY OF THE INVENTION

One aspect of the present invention pertains to methods of purification of an organic lithium salt comprising the steps of: (a) dissolving an impure organic lithium salt in a solution comprising an organic complexing solvent; (b) crystallizing from said solution a solid solvate complex comprising said lithium salt and said organic complexing solvent; (c) separating said solid solvate complex from said solid solution; (d) dissociating said solid solvate complex to yield: (i) said lithium salt in a solid form, and, (ii) a volatile composition comprising said organic complexing solvent; and, (e) removing said volatile composition to yield said lithium salt in a solid form of purity greater than the purity of said impure lithium salt.

In one embodiment, the organic complexing solvent forms a moderately strong solvate complex with said lithium salt.

In one embodiment, the organic complexing solvent comprises an ether.

In one embodiment, the organic complexing solvent comprises an ether selected from the group consisting of: aliphatic dialkyl ethers and cyclic ethers.

In one embodiment, the aliphatic diallyl ether is selected from the group consisting of: dimethyl ether, ethylmethyl ether, diethyl ether, methylpropyl ether, dipropyl ether, methylisopropyl ether, diisopropyl ether, methylbutyl ether, dibutyl ether, methyl t-butyl ether, methylhexyl ether, methyloctyl ether, and di-(2-ethylhexyl)ether. In a preferred embodiment, the aliphatic dialkyl ether is diethyl ether.

In one embodiment, the cyclic ether is selected from the group consisting of: tetrahydrofiiran, 3-methyltetrahydrofiran, tetrahydropyran, dihydropyran, oxepane, furan, 1,4-dioxane, 1,4-dioxepane, oxocane, and 1,4-dioxocane. In a preferred embodiment, the cyclic ether is 1,4-dioxane.

In one embodiment, the lithium salt is a lithium salt with an anion selected from the group consisting of: alkylcarboxylates, arylcarboxylates, alkylsulfonates, arylsulfonates, phenolates, amides, fluoroalkylsulfonyl imides, fluoroalkylsulfonyl methides, fluoroalkylsulfonates, In a preferred embodiment, the lithium salt is lithium bis(trifluoromethylsulfonyl)imide, Li(CF$_3$SO$_2$)$_2$N.

In one embodiment, the solid solvate complex comprises lithium bis(trifluoromethylsulfonyl)imide and 1,4-dioxane.

In one embodiment, the solid solvate complex comprises lithium bis(trifluoromethylsulfonyl)imide and diethyl ether.

In one embodiment, the solid solvate complex comprises lithium bis(trifluoromethyl sulfonyl) imide and an ether selected from the group consisting of: aliphatic dialkyl ethers and cyclic ethers.

In another embodiment of the method of this invention, after step (a) and before step (b), the solution is filtered to remove un-dissolved solids.

In one embodiment, the organic complexing solvent comprises a mixture of two organic complexing solvents. In one embodiment, the volume ratio of said complexing solvents in said mixture is from 1:10 to 10:1. In one embodiment, the volume ratio of said complexing solvents in said mixture is from 1:5 to 5:1. In one embodiment, the volume ratio of said complexing solvents in said mixture is from 1:3 to 3:1.

In one embodiment, the solution further comprises a non-complexing solvent. In one embodiment, the non-complexing solvent is a hydrocarbon solvent selected from the group consisting of: aromatic hydrocarbons, aliphatic hydrocarbons and alicyclic hydrocarbons.

In one embodiment, the aromatic hydrocarbon is selected from the group consisting of: toluene, o-xylene, p-xylene, m-xylene, mesitylene, methylethylbenzene, diethylbenzene, isopropylbenzene, diisopropylbenzene, chlorobenzene, and dichlorobenzene.

In one embodiment, the aliphatic hydrocarbon is selected from the group consisting of: pentane, hexane, heptane, octane, nonane, decane, isopentane, isohexane, and isooctane.

In one embodiment, the alicyclic hydrocarbon is selected from the group consisting of: cyclopentane, cyclohexane, cycloheptane, methylcyclopentane, methylcyclohexane, and cyclooctane.

In one embodiment, the volume ratio of the combined total volume of said complexing solvent to the combined total volume of non-complexing solvent present is from 10:1 to 1:10. In one embodiment, the volume ratio of the combined total volume of said complexing solvent to the combined total volume of noncomplexing solvent present is from 5:1 to 1:5. In one embodiment, the volume ratio of the combined total volume of said complexing solvent to the combined total volume of non-complexing solvent present is from 3:1 to 1:5.

In another embodiment of the method of this invention, after step (a) and before step (b), crystallization of the solvate complex is initiated by the addition of a non-complexing solvent. In one embodiment, the non-complexing solvent is a hydrocarbon. In one embodiment, the non-complexing solvent is a hydrocarbon selected from the group consisting of: aromatic hydrocarbons, aliphatic hydrocarbons and alicyclic hydrocarbons.

In one embodiment, the solid solvate complex is dissociated into the lithium salt in a solid form of higher purity by heating the solid solvate complex under vacuum at a temperature below the melting point of the solvate complex. In a preferred embodiment, the temperature is 20° C. or more below the melting point of the solvate complex.

Another aspect of the present invention pertains to a solid solvate complex for use in the purification of an organic lithium salt, wherein said solid solvate complex comprises an organic lithium salt and an organic complexing solvent, wherein said organic lithium salt is selected from the group consisting of: lithium fluoroalkylsulfonylimides, lithium fluoroalkylsulfonates, lithium fluoroalkylsulfonylmethides, wherein said organic complexing solvent comprises an ether.

In one embodiment, the ether is a aliphatic dialkyl ether selected from the group consisting of: dimethyl ether, ethylmethyl ether, diethyl ether, methylpropyl ether, dipropyl ether, methylisopropyl ether, diisopropyl ether, methylbutyl ether, dibutyl ether, methyl t-butyl ether, methylhexyl ether, methyloctyl ether, and di(2-ethylhexyl) ether. In one embodiment, the ether is a cyclic ether selected from the group consisting of: tetrahydrofuran, 3-methyltetrahydrofuran, tetrahydropyran, dihydropyran, oxepane, fuiran, 1,4-dioxane, 1,4-dioxepane, oxocane, and 1,4-dioxocane.

Yet another aspect of the present invention pertains to a nonaqueous electrolyte for use in an electric current producing cell, said electrolyte comprising a lithium salt and a nonaqueous solvent, wherein said lithium salt is purified by the method of this invention prior to use in said electrolyte. In one embodiment, said electrolyte is selected from the group consisting of: liquid electrolytes, gel polymer electrolytes and solid electrolytes.

Still another aspect of the present invention pertains to an ink jet ink composition comprising a liquid carrier medium and a lithium salt, wherein said lithium salt is purified by the method of this invention prior to use in said composition.

BRIEF DESCRIPTION OF DRAWINDS

DETAILED DESCRIPTION OF THE INVENTION

Methods of Purification

One aspect of the present invention pertains to methods of purification of an organic lithium salt comprising the steps of: (a) dissolving an impure organic lithium salt in a solution comprising an organic complexing solvent; (b) crystallizing from said solution a solid solvate complex comprising said lithium salt and said organic complexing solvent; (c) separating said solid solvate complex from said solution; (d) dissociating said solid solvate complex to yield: (i) said lithium salt in a solid form, and, (ii) a volatile composition comprising said organic complexing solvent; and, (e) removing said volatile composition to yield said lithium salt in a solid form of purity greater than the purity of said impure lithium salt.

In one embodiment, the organic complexing solvent comprises an ether. In one embodiment, the lithium salt is lithium bis(trifluoromethylsulfonyl)imide.

The purification methods of the present invention may be adapted to a wide variety of lithium salts. These methods of purification are particularly usefuil for the purification of ionic organic lithium salts, used as ionic electrolyte salts in the electrolytes of electrolytic cells, primary batteries, rechargeable batteries, fuiel cells and the like.

Solvate Complexes

The term "solvent", as used herein, pertains to a substance, usually a liquid, in which another substance, usually a solid, may be dissolved. A solvent may comprise a single chemical compound (e.g., pure ethyl alcohol) or it may comprise a mixture of chemical compounds (e.g., ethyl alcohol and ethyl acetate).

The term "solute", as used herein, pertains to a substance which has been dissolved in a solvent to yield a solution. The solute is usually the component of a solution which is present in a lesser amount than the solvent.

The term "solvation", as used herein, pertains to a chemical interaction between a solute and a solvent in a solution, which typically is in the form of coordinate bonds which are usually weaker than covalent bonds.

The term "solvate" and "solvate complex", as used herein, pertain to the product of the chemical interaction between a solute and one or more solvent molecules, in which the solute and solvent molecules are bound by coordinate bonds.

Solvate complexes may vary in stability. For example, solvate complexes such as hydrates may be readily isolated as crystalline solids in which the solvent is very difficult to remove from the solute. Other solvate complexes are very loose associations of the solute and solvent which can be detected in solution but are too unstable to be isolated from solution. Still other solvate complexes possess stability intermediate in nature such that they can be isolated but on the other hand may be subsequently dissociated into solid and solvent without much difficulty.

Many materials form solvate complexes upon dissolution in a solvent. Especially well known are hydrates of inorganic salts formed upon dissolution in water, such as, for example copper sulfate, as described in *Advanced Inorganic Chemistry*, 3$^{rd}$ Edition, (1972), page 917, John Wiley & Sons, by Cotton and Wlkinson. As alkali metal cations have a particularly strong affinity for oxygen containing organics, especially ethers or polyethers, these cations may form stable and isolable solvate complexes with these solvents (for example, see Cotton and Wilkinson, loc. Cit. page 199). Polyethers, such as, dimethoxyethane (glyme), or the dimethyl ether of diethyleneglycol (diglyme) and higher glymes (e.g., triglyme, tetraglyme), are typical examples of ethers which form stable solvate complexes. For example, U.S. Pat. No. 4,321,314 to Bowden et aL describes avery stable solvate complex formed between glyme and $LiClO_4$. Cyclic polyethers, such as those referred to as crown ethers, form even stronger complexes with alkali metal cations as described, for example, in U.S. Pat. Nos. 3,562,295, 3,687, 978 and 3,987,061 to Pedersen. On the other hand, an example of a slightly stable solvate complex is provided by sodium carbonate decahydrate crystals ($Na_2CO_3 \cdot 10H_2O$), which upon standing at ambient temperature and pressure rapidly lose water of solvation (often termed efflorescence).

The terms "stable" and "stability", as used herein, in the context of solvate complexes pertains to the degree to which such complexes may be isolated as a compound, that is, a compound of solute and solvent, usually in solid form.

The terms "moderately stable" and "moderate stability", as used herein in the context of solvate complexes, pertains to such complexes which can be isolated as a compound, that is, a compound of solute and solvent, usually in solid form, which isolated compound can then be dissociated to yield solid solute, under vacuum at a temperature less than the melting point of the isolated compound and less than the melting point of the solute. Moderately stable solvate complexes melt at a temperature greater than ambient temperature (i.e., 20° C.), preferably at a temperature from about 40° C. to about 250° C., more preferably at a temperature from about 60° C. to about 220° C., still more preferably at a temperature from about 75° C. to about 200° C.

Lithium salts have been shown to form solvate complexes with a number of solvents. U.S. Pat. No. 3,977,900 to Luehrs describes the formation and isolation of LiCl●HMPA, LiBr●4HMPA, LiBr●TMU, $LiClO_4$●HMPA, $LiClO_4$●4HMPA, among others, where HWA is hexamethylphosphoramide and TMU is tetramethylurea Couture et al., *Canadian Journal of Chemistry*, 1996, 74, 153–164, describe the identification of lithium salt solvate complexes $LiClO_4$●2DME, LiBr●3BUTY and LiBr●2DME, where DME is dimethoxyethane and BUTY is butyrolactone. Olsher et al., *Chemical Reviews*, 1991, 91, 137–164, summarize the coordination chemistry of lithium, and review the crystal and molecular structure of lithium salts. Numerous examples in which solvent molecules are incorporated into crystalline lithium salts are given in the review. Snaith and Wright in Chapter 8 entitled "Complexes of Inorganic Lithium Salts" in *Lithium Chemistry*, (1995), pp. 227–293, Eds. Sapse and von Schleyer, Wiley-Interscience, summarize data on additional examples of lithium solvate complexes. Brouillette et al., *Journal of Solution Chemistry*, 1998, 27, 151–182 report that, based on the phase diagram, lithium bis(trifluoromethylsulfonyl)imide forms a stable solvate complex with dimethoxyethane which melts at 29° C.

The dissolution of a solute in a solvent may lead to a single solvate complex (solute+solvent), for example, $M(Sol)_4$, but in many cases the result is a family of solvate complexes such as $M(Sol)$, $M(Sol)_2$, $M(Sol)_3$, $M(Sol)_4$, $M(Sol)_5$, $M(Sol)_6$, $M(Sol)_n$, etc., where M is the solute molecule and Sol, the solvating entity, is the solvent, and n is an integer from 7 to about 20. For a specific combination of solute and solvent, one or more solvate complexes may coexist or be in equilibrium with each other. Although several solvate complexes may exist in solution at any time, it may be possible to isolate only solvate complexes of some specific solvent/solute ratios as stable compositions from solution. For example, three or two or one or even none of the solvate complexes may be isolable. Isolation of solid from solution, on the other hand, may lead to a solid containing more than one solvate complex, such as, for example, a mixture of $M(Sol)_2$ and $M(Sol)_4$. It is fther possible that isolation of solvate complex may lead to a mixture of solvated material and unsolvated material, such as, for example, a mixture of $M(Sol)_2$ and M.

Complexing Solvents

The term "complexing solvent", as used herein, pertains to a solvent which forms one or more coordination bonds with a solute ion to form a solvate complex.

Lithium ions (ie., $Li^+$) may participate in solvate complex formation with many solvents which contain donor atoms. Solvents which contain the donor atoms N and O are especially effective in forming solvate complexes with lithium ions. In the methods of the present invention, solvents containing O atom donors which can form Li—O coordination bonds are particularly preferred.

Examples of oxygen containing complexing solvents which form Li—O coordination bonds include, but are not limited to, carboxylic acid esters, carbonate esters, ketones, aldehydes, lactones, alcohols, ethers, sulfoxides, phospbine oxides, trialkylphosphate esters, triarylphosphate esters and phosphoramidates. The complexing solvents containing O donor atoms which are most preferred include, but are not limited to, ethers and polyethers, and particularly aliphatic or cyclic ethers.

Examples of suitable ethers for use as complexing solvents include, but are not limited to, the following aliphatic dialkyl ethers:

(a) dimethyl ether,
   CH₃—O—CH₃
(b) methylethyl ether,
   CH₃—O—CH₂CH₃
(c) methylpropyl ether,
   CH₃—O—CH₂CH₂CH₃
(d) methylisopropyl ether,

(e) diethyl ether,
   CH₃CH₂—O—CH₂CH₃
(f) dipropyl ether,
   CH₃CH₂CH₂—O—CH₂CH₂CH₃
(g) diisopropyl ether,

(h) dibutyl ether,
   CH₃CH₂CH₂CH₂—O—CH₂CH₂CH₂CH₃
(i) diisobutyl ether, j) metlyl n-butyl ether,
   CH₃—O—CH₂CH₂CH₂CH₃
(k) methyl t-butyl ether,

(l) methylhexyl ether and,
   CH₃—O—CH₂CH₂CH₂CH₂CH₂CH₃
(m) bis-2-ethylhexyl ether.

Additional examples of suitable ethers for use as complexing solvents include, but are not limited to, the following cyclic ethers:
   (a) tetrahydrofluran, (b) 3-methyltetrahydrofuran,

(c) dihydropyran,

(d) tetrahydropyran,

(e) 1,4-dioxane,

(f) oxepane,

(g) 1,4-dioxepane, (h) oxocane, and, (i) 1,4-dioxocane

Mixtures of two or more complexing solvents may also be used as the complexing solvent in the methods of this invention. For example, mixtures of dialkyl ethers, of dialkyl ethers and cyclic ethers, or of cyclic ethers may be used as the complexing solvent. The solvate complexes formed from these complexing solvent mixtures may contain some or all components of the mixture as part of the solvate complex composition.

When a mixture of two different complexing solvents is used, suitable volume ratios of the complexing solvents in the methods of the present invention include, but are not limited to, the range of 1:10 to 10:1. In one embodiment, the volume ratio of the complexing solvents in the methods of the present invention is in the range of 1:5 and 5:1. In one embodiment, the volume ratio of the complexing solvents is in the range of 1:3 to 3:1.

The composition of a solvate complex formed from such mixtures of complexing solvents can be represented as $M(Sol)_n(Sol')_m$, where M represents the ionic solute and Sol and Sol' represent the different complexing solvents forming a solvate complex and, n and m may be the same or different and are integers from 0 to about 10, and the sum of n and m is an integer from 2 to about 10.

Many polyethers, such as dimethoxyethane, dimethyl ether of diethylene glycol (diglyme) and higher glymes (e.g., triglyme, tetraglyme), solvate lithium ions strongly and are not preferred in the methods of the present invention. Other oxygen containing polar aprotic solvents such as dioxolane, dimethyl carbonate, diethyl carbonate, ethylene carbonate, and propylene carbonate also solvate lithium ions strongly and are not preferred.

The specific choice of complexing solvents preferred for use in the methods of this invention is based on the formation with the lithium salt of a solvate complex with a melting point greater than 40° C. (and typically less than about 250° C.). In one embodiment, the melting point of the solvate complex is greater than 60° C. In one embodiment, the melting point of the solvate complex is greater than 90° C. It is further preferred that the solvate complex dissociates into the pure salt and the volatile complexing solvent under vacuum at a temperature below the melting point of the solvate complex. It is still further preferred that the complexing solvent have a boiling point at least 10° C. below the temperature of dissociation of the solvate complex under the conditions of vacuum used. Preferred complexing solvents for use in the method of this invention are complexing solvents which have a boiling point below 70° C. at 10 mm of Hg (~1333 Pa). The specific choice of complexing solvent to achieve the desired melting point in the solvate complex is also dependent on the anion associated with the lithium cation.

With the above general criteria and examples in mind, one of skill in the art is readily able to choose an appropriate complexing solvent.

Lithium Salts

The organic lithium salts that may be purified by the methods of this invention include, but are not limited to, those lithium salts with anions selected from the group consisting of:

(a) alkylcarboxylates,

(b) arylcarboxylates,

(c) alkylsulfonates, (d) arylsulfonates, (e) tetraphenylborate;

(f) alkoxides;
R—O⁻

(g) phenoxides;

(h) enolates;

(i) thiolates;
R—S⁻

(k) diisopropylamide;

(l) bis(trimethylsilyl)amide;

(m) bis(triphenylsilyl)amide;

(n) trifluoromethyl sulfonate, (triflate);

(o) bis(trifluoromethylsulfonyl) imide; and,

(q) tris(trifluoromethylsulfonyl) methide, (methide)

where R is any alkyl or substituted alkyl, including but not limited to, $C_1$ to $C_{18}$ linear, branched or alicyclic alkyl groups (including, but are not limited to, methyl, ethyl, propyl, isopropyl, butyl, and higher analogs, with or without halogen substituents, such as fluoro, chloro and bromo) and Ar is any aryl or substituted ayl group (including but not limited to, phenyl and naphthyl groups, and substituted derivatives thereof).

Additional lithium imide salts that may be purified by the methods of this invention are described in U.S. Pat. No. 5,514,493, to Waddell et al, by Krause et al. in *Journal of Power Sources*, 1997, 68, 320–325 and by Kita et al. in *Journal of Power Sources*, 1997, 68, 307–310.

Still other lithium salts that may be purified by the methods of this invention are:

and lithium salts disclosed in U.S. Pat. No. 5,538,812 to Lee et al.

The preferred organic lithium salts that may be purified by the methods of this invention are those selected from the groups, lithium carboxylates, lithium enolates, lithium phenolates, lithium thiolates, lithium sulfonates, lithium fluoroalklylsulfonylimides, lithium fluoroalkylsulfonates and lithium fluoroalkylsulfonylmethides.

Most preferred organic lithium salts that may be purified by the methods of this invention are lithium bis (trifluoromethylsulfonyl)imide and lithium tris (trifluoromethylsulfonyl)methide.

Solvate Complex Formation

The method of formation of the solvate complex is by dissolution of the impure lithium salt in the complexing solvent or mixture of complexing solvents at a temperature at or close to the boiling point of the solvent or solvent mixture. The amount of complexing solvent is such that a saturated or nearly saturated solution of the salt and complexing solvent is formed. Impurities insoluble in the solvent or solvent mixture may optionally be removed by filtration of the hot solution. The solution is then cooled, the solvate complex crystallizes and is separated by filtration. The solution may be cooled to a temperature close to the ambient (e.g., 20 to 25° C.) or to a sub-ambient temperature (e.g., 0° C. or below). Alternatively, if the solvate complex does not crystallize readily, a non-complexing solvent such as a hydrocarbon may be added to induce crystallization of the solvate complex.

Suitable non-complexing solvents are liquid hydrocarbons, and include, but are not limited to, aliphatic, alicyclic, and aromatic hydrocarbons. Examples of suitable aliphatic hydrocarbon solvents, which may be linear or branched, include, but are not limited to, pentane, hexane, heptane, octane, nonane, decane, isopentane, isohexane, isoheptane, isooctane and higher homologs. Examples of alicyclic hydrocarbons include, but are not limited to, cyclopentane, cyclohexane, cycloheptane, alkylated derivatives of the foregoing and higher homologs. Examples of suitable aromatic hydrocarbons include, but are not limited to, toluene, xylenes, mesitylene, ethylbenzene, methylethylbenzene, isopropylbenzene, diisopropylbenzene, chlorobenzene, and dichlorobenzene.

The volume ratio of the combined total of complexing solvent to the combined total volume of non-complexing solvent in the methods of the present invention include, but are not limited to, 10:1 to 1:10. In one embodiment, the volume ratio of the combined total volume of complexing solvent to the non-complexing solvent is from 5:1 to 1:5. In one embodiment, the volume ratio of the combined total volume of complexing solvent to the combined total volume of non-complexing solvent is from 3:1 to 1:5.

The solvate complex may optionally be further purified by recrystallization. Preferably, the recrystallizing solvent is a complexing solvent (for example, the preferred ether solvents), more preferably the complexing solvent of the solvate complex.

Solvate Complex Dissociation

One step in the methods of the present invention involves dissociating the solid solvate complex to yield: (i) the lithium salt in a solid form and, (ii) a volatile composition comprising the organic complexing solvent.

The term "volatile composition", as used herein, relates to a volatile liquid (that is, a liquid with a substantial vapor pressure at the applied pressure) or a mixture of a volatile liquid and its vapor.

The preferred method for obtaining the purified lithium salt from the solvate complex is by heating the solvate complex under vacuum at a temperature below the melting point of the solvate complex. A preferred temperature is about 35° C. below the melting point of the solvate complex. A more preferred temperature is about 20° C. below the melting point of the solvate complex.

Most preferred is to follow a heating schedule in which the temperature is increased at time intervals, but always to a temperature about 20° C. below the melting point of the solvate complex present at that particular time. As solvating solvent is removed from the solvate complex, the melting point of remaining solvate complex typically increases allowing a stepwise or gradual increase in the dissociation temperature. Typical heating times at any set temperature are from about 4 to about 24 hours. For example, the solvate complex may be heated at less than 50° C. for 4 hours, then at 70 DC for 6 hours, and finally at 100° C. for 24 hours. Many variations can be made on the heating progression as long as the temperature remains about 20° C. below the melting point of the solvate complex throughout the dissociation process.

Purity

Impurities in ionic organic lithium salts may arise in their preparation from incomplete reaction, from side reactions, from impurities present in reactants, and from incomplete a removal of reactants, catalysts or reaction media such as solvents. Packaging materials may represent another source of impurities, for example, plasticizers leached from containers or inadvertent contamination. Examples of impurities that may be present in organic lithium salts include, but are not limited to, free acids, such as carboxylic acids, sulfonic acids, perfluoroalkylsulfonic acids, inorganic anions such as fluoride, chloride, bromide, or carbonate, cations such as calcium, magnesium, sodium, potassium, aluminum, ammonium, tetraalkylammonium, and neutral organic compounds, such as esters, aldehydes, ketones or alcohols. Impurity levels impacting the intended use may range from as low as 1 ppm to about 1000 ppm (0.1%) to as high as 1% to about 5%.

The purity of the lithium salt can be measured by a variety of methods, as known to one skilled in the art, appropriate to the intended use of the purified salt and the nature of the impurities originally present in the salt. For example, one assay method for lithium salts to be used as electrolytes in batteries is Differential Scanning Calorimetry (DSC). Spectroscopic techniques such as NMR (nuclear magnetic resonance) for nuclei such as $C^{13}$, $H^1$, $F^{19}$, $Li^7$, and $P^{31}$ can be used to determine purity. Other methods include, but are not limited to, elemental analysis or an analysis for specific trace elements or ions. For example, atomic absorption spectroscopy or ICP would be appropriate for trace metal analysis.

In one embodiment, the purified lithium salt has a purity which is at least 0.5% greater than the purity of the impure lithium salt from which it was derived (e.g., a change in purity from 99% to 99.5% corresponds to an increase of 0.5/99~0.5%). In one embodiment, the purified lithium salt has a purity which is at least 1% greater (e.g., a change in purity from 98% to 99% corresponds to an increase of 1/98~1%). In one embodiment, the purified lithium salt has a purity which is at least 5% greater. In one embodiment, the purified lithium salt has a purity which is at least 10% greater. In one embodiment, the purified lithium salt has a purity which is at least 15% greater. In one embodiment, the purified lithium salt has a purity which is at least 20% greater.

Yield

The methods of the present invention facilitate the purification of lithium salts in high yield. In one embodiment, the yield (calculated as the ratio of weight of the purified lithium salt to the weight of the impure lithium salt from which it was derived and reported as a percentage) is at least about 70% (e.g., 100 g of impure starting material yields 70 g of purified product). In one embodiment, the yield is at least about 80%. In one embodiment, the yield is at least about 85%. In one embodiment, the yield is at least about 90%. In one embodiment, the yield is at least about 95%.

Uses of Purified Lithium salts

Lithium salts purified by the methods of the present invention may be utilized in a variety of applications where purity is important, including, but not limited to, applications where optical or electrical properties are important They are particularly useful when incorporated as the ionic electrolyte salt into nonaqueous electrolyte compositions to improve the performance of electric current producing cells. The electrolyte compositions may be any of the types of electrolytes known in the art, including, but not limited to, liquid electrolytes, gel polymer electrolytes, and solid polymer electrolytes. The purified lithium salts of the present invention may also find application in ink jet ink compositions comprising a lithium salt, and a liquid carrier medium. The lithium salt is typically the lithium salt of an anionic dye colorant with sulfonate or carboxylate fimctional groups. The liquid carrier medium is water or organic solvents or combinations thereof, as known in the art of ink jet printing applications. Choice of the specific liquid carrier medium depends on the specific ink jet printer and its compatible ink jet printing head and cartridge being used for the ink jet printing.

EXAMPLES

Several embodiments of the present invention are described in the following examples, which are offered by way of illustration and not by way of limitation.

Example 1

Figure 1:
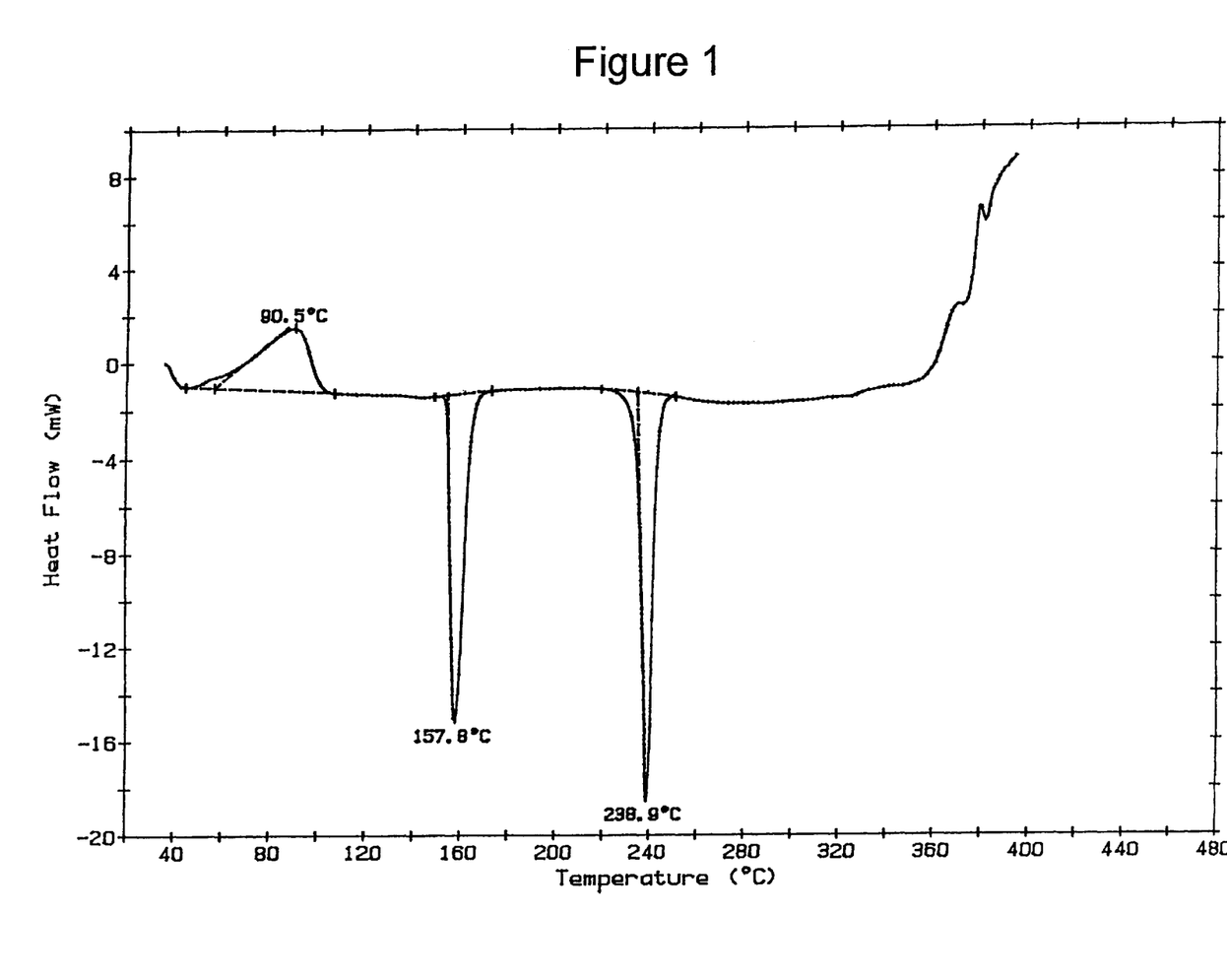
FIG. 1 shows the Differential Scanning Calorimetry (DSC) spectrum of impure lithium bis(trifluoromethylsulfonyl)imide.

Impure commercially available lithium bis (trifluoromethylsulfonyl)imide, ($Li(CF_3SO_2)_2N$, 100 g), (available from 3M Corporation, St. Paul, Minn.), whose DSC curve is shown in FIG. 1, was added, with stirring, to 1,4-dioxane, ($C_4H_8O_2$, 300 mL), and stirred at room temperature for 5 minutes before heating to 80° C. until all the salt dissolved. The solution was allowed to cool to room temperature and held for 12 hours before filtration of the crystals of solvate complex which had separated. The collected crystals were washed with 100 mL of a dioxanelhexane (4:1 by volume) mixture.

The solvate complex crystals were dried for 3 hours under vacuum at room temperature losing some of the solvating dioxane. Yield, after drying, was 124 g , melting point 143.7° C. Elemental analysis of the solvate complex gave: 18.44% S. 4.17% N, 1.93% Li. The calculated values were: 15.27% S, 3.34%N, 1.67% Li for a lithium bis (trifluoromethylsulfonyl) imide/1,4-dioxane molar ratio of 2:3,(i.e., $2Li(CF_3SO_2)_2N3\ C_4H_8O_2$).

Additional solvate complex was obtained as follows. Hexane (300 mL) was added to the mother liquor remaining after the first crystallization and the solution heated to 80° C., allowed to cool to room temperature and left for 12 hours. Filtration of the solid crystallized from solution and drying at room temperature under vacuum yielded an additional 12.8 g of solvate complex crystals.

The hexane/dioxane filtrate mother liquor was evaporated to dryness and carefully heated flrther under vacuum to remove all solvent traces to yield 3.9 g of solid. This solid contained the concentrated impurities from the original lithium bis(trifluoromethylsulfonyl)imide.

Example 2

Figure 3:
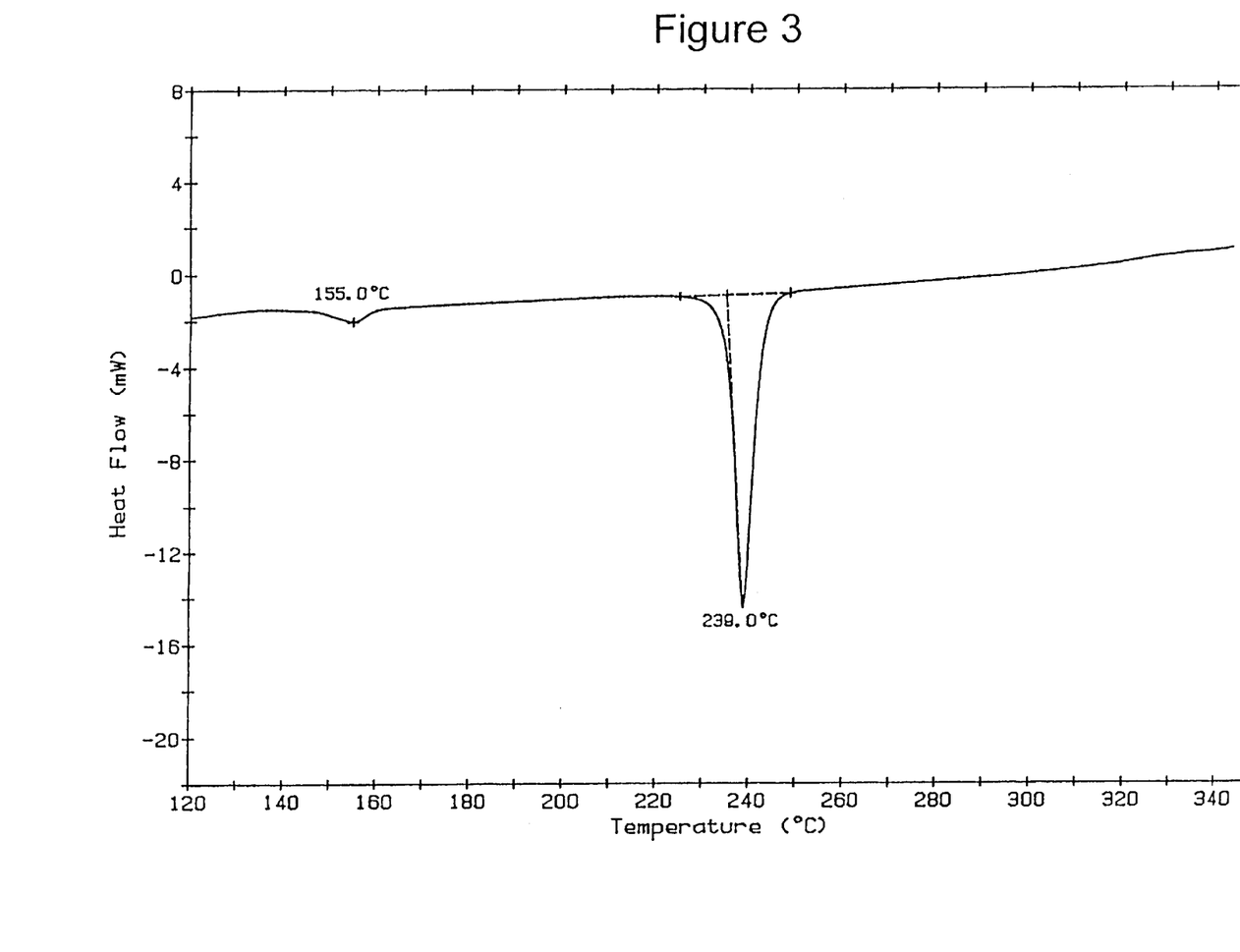
FIG. 3 shows the Differential Scanning Calorimetry (DSC) spectrum of pure lithium bis(trifluoromethylsulfonyl)imide formed by the thermal dissociation of the solvate complex of lithium bis(trifluoromethylsulfonyl)imide with 1,4-dioxane.

The solvate complex crystals from Example 1, 136.8 g, (124 g +12.8 g), were heated in a vacuum oven as follows: 100° C. for 6 hours, 120° C. for 12 hours and finally 12 hours at 140° C. The pure lithium bis (trifluoromethylsulfonyl) imide, 95.7 g (96% yield) was obtained as a white crystalline solid, melting point 239° C., as shown in the DSC of FIG. 3.

Example 3

Figure 2:
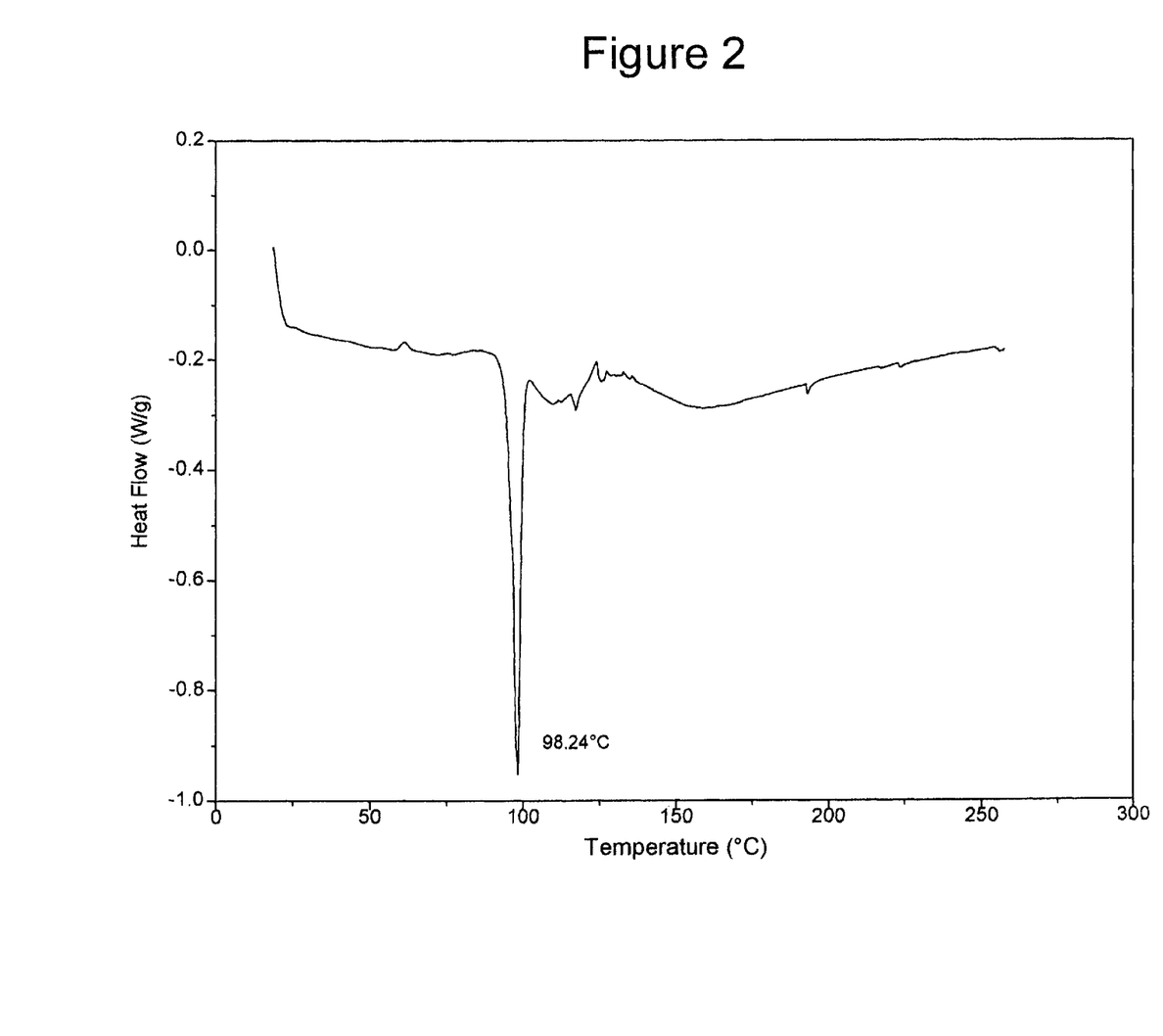
FIG. 2 shows the Differential Scanning Calorimetry (DSC) spectrum of the solvate complex of lithium bis(trifluoromethylsulfonyl)imide with 1,4-dioxane.

Impure commercially available lithium bis (trifluoromethylsulfonyl)imide (100 g), as in Example 1, was added, with stirring, to 1,4Aioxane (300 mL), and stirred at room temperature for 5 minutes before heating to 80° C. until all the salt dissolved. The solution was allowed to cool to room temperature and held for 12 hours before filtration of the crystals of solvate complex which had separated. The collected crystals were washed with a dioxane/hexane (4:1 by volume) mixture and were found to have melting point 98.2° C. by DSC as shown in FIG. 2.

Elemental analysis of the crystallized solvate complex, melting point 98.2° C., without any vacuum drying, gave: 26.35% C, 15.27% S, 3.32% N. The calculated values were: 25.92% C, 13.82% S, 3.02% N for a lithium imide/1, 4dioxane molar ratio of 1:2, (i.e., $Li(CF_3SO_2)_2N2\ C_4H8O_2$).

The solvate complex crystals were heated in a vacuum oven by the procedure of Example 2 to yield pure lithium bis(trifluoromethylsulfonyl)imide.

Example 4

Impure commercially available lithium bis (trifluoromethylsulfonyl)imide ($Li(CF_3SO_2)_2N$, 59 g) was dissolved in diethyl ether ($C_4H_{10}O$, 120 mL). After filtration the solution was added to dry o-xylene (200 mL) in a round bottom flask heated in an oil bath. As the internal temperature increased from 85° C. to 108° C., distillate was removed and the flask contents become turbid. With continued heating the internal temperature was gradually increased to 140° C. and, as distillation continued, crystals were formed. Heating was stopped when the temperature of distillation reached 135° C. After cooling the flask was transferred to a glove box and the crystals, the diethyl ether solvate complex of lithium bis(trifluoromethylsulfonyl)imide, were filtered and washed with hexane. The solvate was dissociated by heating under vacuum at 125° C. for 4 hours. Yield of pure lithium bis(trifluoromethylsulfonyl)imide was 52.9 g (52.9/ 59~90%).

Example 5

Impure commercially available lithium bis (trifluoromethylsulfonyl)imide ($Li(CF_3SO_2)_2N$, 54.5 g) was dissolved in diethyl ether ($C_4H_{10}O$, 69 g). The solution was filtered and placed in an addition finnel. This solution was added dropwise to boiling o-xylene (300 mL) in a flask fitted for distillation. The distillation temperature immediately was lower as the ether distilled. After the addition was completed, the distillation temperature rose to the boiling point of xylene and distillation was halted. The crystalline solid, the diethyl ether solvate complex of the lithium bis(trifluoromethylsulfonyl)imide which had formed, was filtered and washed with hexane. Heating overnight (16 hours) under vacuum at 125° C. yielded pure lithium bis (trifluoromethylsulfonyl)imide as a white solid.

Example 6

A cathode was prepared with a composition by weight of 60% elemental sulfur (available from Aldrich Chemical Company, Milwaukee, Wis.), 20% non-activated carbon nanofibers (PYROGRAF-III, a trademark for carbon nanofibers available from Applied Sciences, Inc., Cedarville, Ohio.), 10% conductive carbon pigment (PRINTEX XE-2, a trademark for a carbon pigment available from Degussa Corporation, Akron, Ohio.), 5% $SiO_2$ (AEROSIL 380, a trademark for a silica pigment available from Degussa Corporation, Akron, Ohio.), and 5% TEFLON dispersion in water/isopropanol (80/20% by weight) with a solids content of 18%. (TEFLON is a trademark for a polytetraluoroethylene polymer available from DuPont Corporation, Wilmington, Del.). The paste was extruded on to aluminum EXMET (a trademark for a metal grid current collector available from EXMET Corporation, Naugatuck, Conn.). The cathode was dried for 1 hour at 60° C. in a vacuum oven. The resulting dry cathode had a thickness of 200 $\mu$m with a total loading of active material of 0.8 g of elemental sulfur per AA cell or 300 mg/cm$^3$ of cathode coating. The surface area per AA cell was 270 cm$^2$.

Wound AA size cells were fabricated from the cathode with a 100 $\mu$m lithimn anode foil and a 25 $\mu$m E25 SETELA separator (a trade mark for a polyolefin separator available from Tonen Corporation, Tokyo, Japan, and also available from Mobil Chemical Company, Films Division, Pittsford, N.Y.).

The cells were filled with a liquid electrolyte of a 1.0 M solution of $LiN(SO_2CF_3)_2$ (with one of (i) the impure lithium salt as received from 3M Corporation, (ii) the lithium salt purified as described in Examples 1 and 2, or (iii) the lithium salt recovered with concentrated impurities from evaporating the mother liquor in Example 1) in 1,3-dioxolane 50%, tetraethyleneglycol dimethylether 20%, dimethoxyefhane 25%, o-xylene 5% (percentages of composition are by volume).

Figure 4:
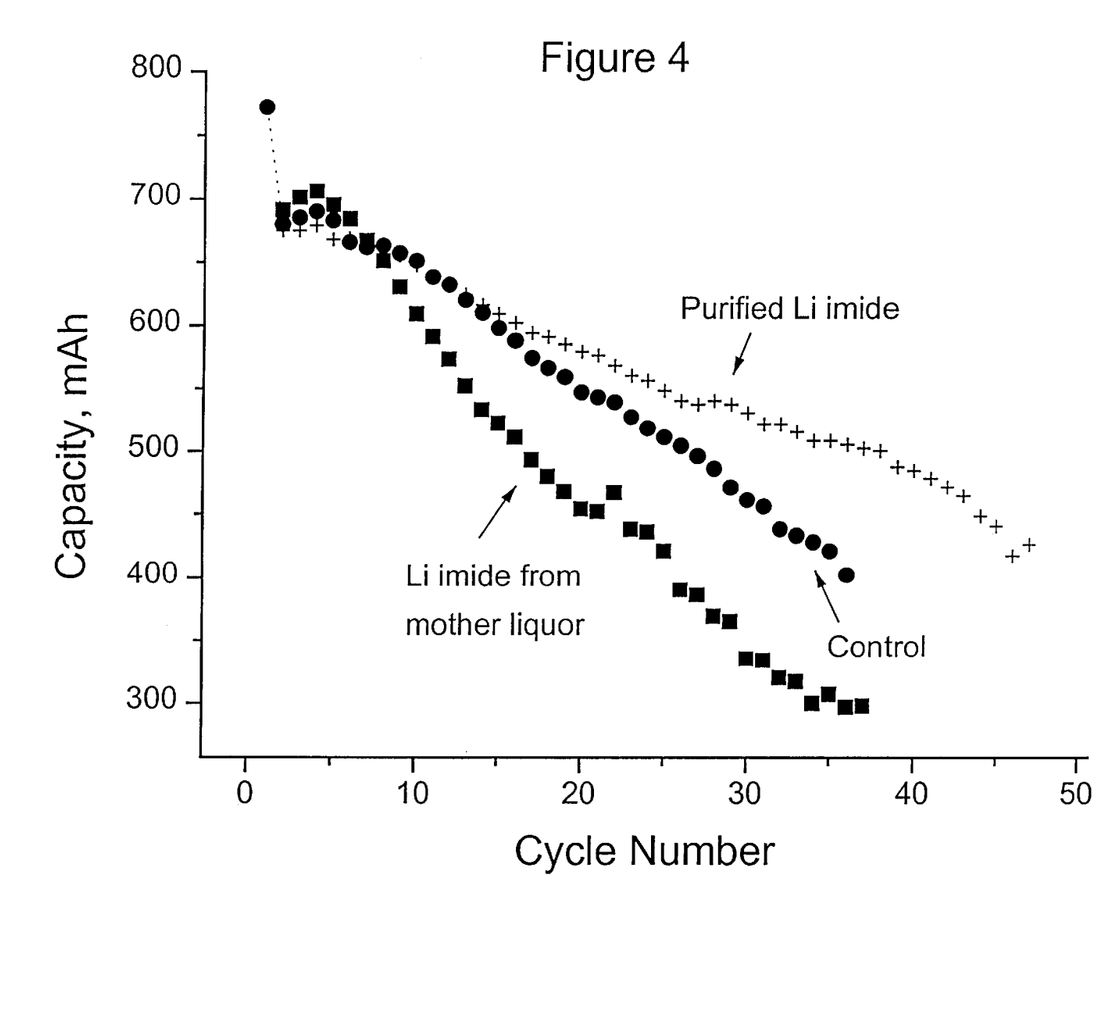
FIG. 4 shows the capacity versus cycle number for a control cell (●)and for cells containing purified lithium imide electrolyte salt ✦ and cells containing lithium imide electrolyte salt from the crystallization mother liquor (■), as described in Example 4.

AA cells using (i) impure lithium bis(trifluoromethylsulfonyl)imide as received from 3M Corporation (control), (ii) purified lithiun bis(trifluoromethylsulfonyl)mide salt (made as described in Example 2), and (iii) lithium bis(trifluoromethylsulfonyl) imide salt recovered with concentrated impurities from evaporating the mother liquor (made as described in Example 1), were tested at a low discharge rate of 0.6 mA/cm² and a charge rate of 0.38 mA/cm², as shown in FIG. 4. The accumulated capacity, calculated from the sum of the discharge capacities at each discharge-charge cycle of the cell until the discharge capacity fell below a cut off value of 500 mAh, was 16.4 Ah (100%) for the control, 23.0 Ah (140%) for the purified lithium bis(trifluoromethylsulfonyl) imide salt, and 10.6 Ah (65%) for the lithium bis(trifluoromethylsulfonyl)imide salt recovered from the mother liquor. Testing of cells with the control salt and the purified salt at a high rate discharge of 1.0 mA/cm² and a charge rate of 0.75 mA/cm² resulted in accumulated capacities of 15.5 Ah (100%) for the control and 17.4 Ah (112%) for the purified salt before reaching the 500 mAh capacity cutoff.

While the invention has been described in detail and with reference to specific embodiments thereof, it will be apparent to one skilled in the art that various changes and modifications can be made without departing from the spirit and scope thereof.

What is claimed is:

1. A method of purification of an organic lithium salt comprising the steps of:
   (a) dissolving an impure organic lithium salt in a solution comprising an organic complexing solvent;
   (b) crystallizing from said solution a solid solvate complex comprising said lithium salt and said organic complexing solvent;
   (c) separating said solid solvate complex from said solution;
   (d) dissociating said solid solvate complex to yield:
      (i) said lithium salt in a solid form, and,
      (ii) a volatile composition comprising said organic complexing solvent; and,
   (e) removing said volatile composition to yield said lithium salt in a solid form of purity greater than the purity of said impure lithium salt.

2. The method of claim 1, wherein the organic complexing solvent forms a moderately strong solvate complex with said lithium salt.

3. The method of claim 1, wherein said organic complexing solvent comprises an ether.

4. The method of claim 1, wherein said organic complexing solvent comprises an ether selected from the group consisting of: aliphatic dialkyl ethers and cyclic ethers.

5. The method of claim 1, wherein said organic complexing solvent comprises an aliphatic dialkyl ether selected from the group consisting of: dimethyl ether, ethylmethyl ether, diethyl ether, methylpropyl ether, dipropyl ether, methylisopropyl ether, diisopropyl ether, methylbutyl ether, dibutyl ether, methyl t-butyl ether, methylhexyl ether, methyloctyl ether, and di-(2-ethylhexyl)ether.

6. The method of claim 1, wherein said organic complexing solvent is diethyl ether.

7. The method of claim 1, wherein said organic complexing solvent comprises a cyclic ether selected from the group consisting of: tetrahydrofuran, 3-methyltetrahydrofuran, tetrahydropyran, dihydropyran, oxepane, furan, 1,4-dioxane, 1,4-dioxepane, oxocane, and 1,4-dioxocane.

8. The method of claim 1, wherein said organic complexing solvent is 1,4-dioxane.

9. The method of claim 1, wherein said lithium salt comprises one or more lithium ions and one or more anions selected from the group consisting of: alkylcarboxylates, arylcarboxylates, alkylsulfonates, arylsulfonates, phenolates, amides, fluoroalkylsulfonil imides, fluoroalkylsulfonyl methides, fluoroalkylsulfonates, and 10. The method of claim 1, wherein said lithium salt is lithium bis(trifluoromethylsulfonyl)imide.

11. The method of claim 1, wherein said solid solvate complex comprises lithium bis(trifluoromethylsulfonyl) imide and diethyl ether.

12. The method of claim 1, wherein said solid solvate complex comprises lithium bis(trifluoromethylsulfonyl) imide and 1,4-dioxane.

13. The method of claim 1, wherein said lithium salt is lithium bis(trifluoromethylsulfonyl)imide, and said solid solvate complex comprises lithium bis(trifluoromethylsulfonyl)imide and an ether selected from the group consisting of: aliphatic dialkyl ethers and cyclic ethers.

14. The method of claim 1, wherein said lithium salt is lithium bis(trifluoromethylsulfonyl)imide, and said solid solvate complex comprises lithium bis(trifluoromethylsulfonyl)imide and an aliphatic dialkyl ether selected from the group consisting of: dimethyl ether, ethylmethyl ether, diethyl ether, methylpropyl ether, dipropyl ether, methylisopropyl ether, diisopropyl ether, methylbutyl ether, dibutyl ether, methyl t-butyl ether, methylhexyl ether, methyloctyl ether and di(2-ethylhexyl) ether.

15. The method of claim 1, wherein said lithium salt is lithium bis(trifluoromethylsulfonyl)imide, and said solid solvate complex comprises lithium bis(trifluoromethylsulfonyl)imide and a cyclic ether selected from the group consisting of: tetrahydrofuran, 3-methyltetrahydofiran, tetrahydropyran, dihydropyran, oxepane, furan, 1,4-dioxane, 1,4-dioxepane, oxocane, and 1,4dioxocane.

16. The method of claim 1, wherein, after step (a) and before step (b), said solution is filtered to remove undissolved solids.

17. The method of claim 1, wherein said organic complexing solvent comprises a mixture of two organic complexing solvents.

18. The method of claim 1, wherein said organic complexing solvent comprises a mixture of two organic complexing solvents, wherein the volume ratio of said two complexing solvents in said mixture is from 1:10 to 10:1.

19. The method of claim 1, wherein said organic complexing solvent comprises a mixture of two organic complexing solvents, wherein the volume ratio of said two complexing solvents in said mixture is from 1:5 to 5:1.

20. The method of claim 1, wherein said organic complexing solvent comprises a mixture of two organic complexing solvents, wherein the volume ratio of said two complexing solvents in said mixture is from 1:3 to 3:1.

21. The method of claim 1, wherein said solution further comprises a non-complexing solvent.

22. The method of claim 1, wherein said solution further comprises a non-complexing solvent, and wherein the volume ratio of the combined total volume of said complexing solvent to the combined total volume of non-complexing solvent present is from 10:1 to 1:10.

23. The method of claim 1, wherein said solution farther comprises a non-complexing solvent, and wherein the volume ratio of the combined total volume of said complexing solvent to the combined total volume of non-complexing solvent present is from 5:1 to 1:5.

24. The method of claim 1, wherein said solution further comprises a non-complexing solvent, and wherein the volume ratio of the combined total volume of said complexing solvent to the combined total volume of non-complexing solvent present is from 3:1 to 1:5.

25. The method of claim 1, wherein said solution further comprises a non-complexing solvent selected from the group consisting of: aromatic hydrocarbons, aliphatic hydrocarbons and alicyclic hydrocarbons.

26. The method of claim 1, wherein said solution further comprises a non-complexing solvent selected from the group consisting of: toluene, o-xylene, p-xylene, m-xylene, mesitylene, methylethylbenzene, diethylbenzene, isopropylbenzene, diisopropylbenzene, chlorobenzene, and dichlorobenzene.

27. The method of claim 1, wherein said solution further comprises a non-complexing solvent selected from the group consisting of: pentane, hexane, heptane, octane, nonane, decane, isopentane, isohexane, and isooctane.

28. The method of claim 1, wherein said solution further comprises a non-complexing solvent selected from the group consisting of: cyclopentane, cyclohexane, cycloheptane, methylcyclopentane, methylcyclohexane, and cyclooctane.

29. The method of claim 1, wherein, after step (a) and before step (b), crystallization of said solvate complex is initiated by the addition of a non-complexing solvent.

30. The method of claim 1, wherein, after step (a) and before step (b), crystallization of said solvate complex is initiated by the addition of a liquid hydrocarbon non-complexing solvent.

31. The method of claim 1, wherein, after step (a) and before step (b), crystallization of said solvate complex is initiated by the addition of a liquid hydrocarbon non-complexing solvent selected from the group consisting of: aromatic hydrocarbons, aliphatic hydrocarbons and alicyclic hydrocarbons.

32. The method of claim 1, wherein said dissociating step comprises heating said solid solvate complex under vacuum at a temperature below the melting point of said solvate complex.

33. The method of claim 1, wherein said dissociating step comprises heating said solid solvate complex under vacuum at a temperature 20° C. or more below the melting point of said solvate complex.

* * * * *